US012521005B2

(12) United States Patent
Roppenecker et al.

(10) Patent No.: US 12,521,005 B2
(45) Date of Patent: Jan. 13, 2026

(54) ENDOSCOPE WITH IMPROVED VIEWING WINDOW CLEANING NOZZLE

(71) Applicant: AMBU A/S, Ballerup (DK)

(72) Inventors: Daniel Bernd Roppenecker, Pürgen (DE); Günter Wilhelm Schütz, Augsburg (DE); Nora Rebekka Tobies, Augsburg (DE)

(73) Assignee: AMBU A/S, Ballerup (DK)

( * ) Notice: Subject to any disclaimer, the term of this patent is extended or adjusted under 35 U.S.C. 154(b) by 294 days.

(21) Appl. No.: 17/922,071

(22) PCT Filed: Apr. 29, 2021

(86) PCT No.: PCT/EP2021/061344
§ 371 (c)(1),
(2) Date: Oct. 28, 2022

(87) PCT Pub. No.: WO2021/219826
PCT Pub. Date: Nov. 4, 2021

(65) Prior Publication Data

US 2023/0165453 A1 Jun. 1, 2023

(30) Foreign Application Priority Data

Apr. 30, 2020 (DE) ..................... 10 2020 111 888.0

(51) Int. Cl.
*A61B 1/12* (2006.01)
*A61B 1/00* (2006.01)
*A61B 1/015* (2006.01)

(52) U.S. Cl.
CPC .......... *A61B 1/126* (2013.01); *A61B 1/00091* (2013.01); *A61B 1/015* (2013.01)

(58) Field of Classification Search
CPC ...... A61B 1/126; A61B 1/00091; A61B 1/015
See application file for complete search history.

(56) References Cited

U.S. PATENT DOCUMENTS 4,898,574 A * 2/1990 Uchiyama ........ A61B 17/32037 606/127
5,339,800 A 8/1994 Wiita et al.
(Continued)

FOREIGN PATENT DOCUMENTS

DE 102010037098 B4 12/2018
JP 08-126605 A 5/1996
(Continued)

OTHER PUBLICATIONS

English translation of JP-2007244796-A (Year: 2007).*
(Continued)

*Primary Examiner* — Michael J Carey
*Assistant Examiner* — Megan Elizabeth Monahan
(74) *Attorney, Agent, or Firm* — Faegre Drinker Biddle & Reath LLP

(57) ABSTRACT

An endoscope including an insertion tube for insertion into a patient's body cavity and a tip at the distal end of the insertion tube, the tip including a tip housing encapsulating an optical inspection device, a viewing window for or of the optical inspection device and a fluid spray nozzle having an outer wall providing a fluid channel surrounded by the outer wall for spraying a fluid onto the viewing window, the fluid spray nozzle having at least one fluid splitting element arranged in the fluid channel for providing a converging fluid flow out of the nozzle onto the viewing window.

21 Claims, 5 Drawing Sheets

(56) References Cited

U.S. PATENT DOCUMENTS

Figure 1:
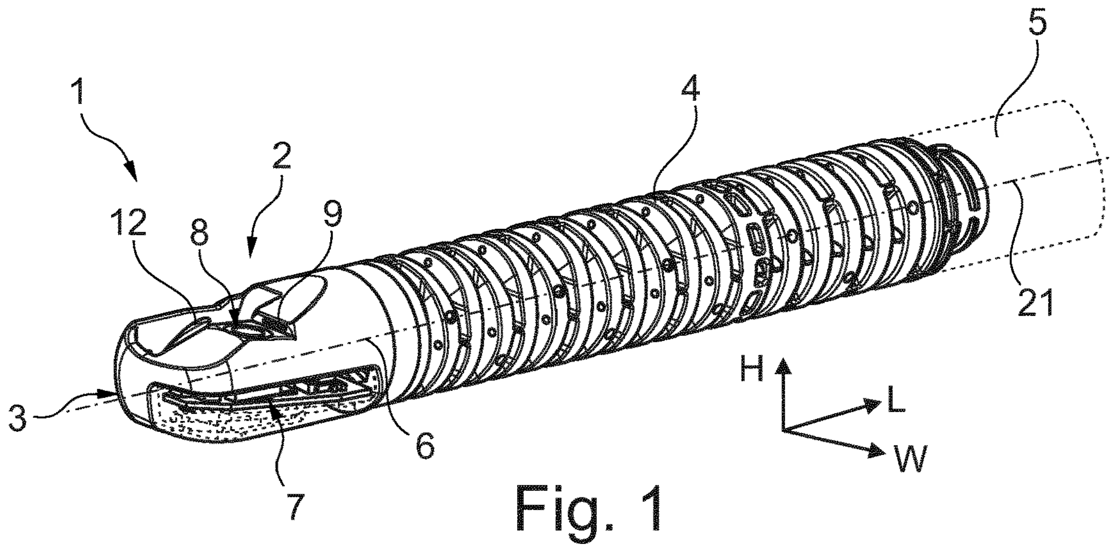

| | | | | |
|---|---|---|---|---|
| 5,944,654 | A * | 8/1999 | Crawford | A61B 1/127 600/128 |
| 6,409,657 | B1 | 6/2002 | Kawano | |
| 6,595,915 | B2 | 7/2003 | Akiba | |
| 8,491,467 | B2 | 7/2013 | Miyamoto et al. | |
| 8,591,406 | B2 | 11/2013 | Hirayama | |
| 2009/0253965 | A1 | 10/2009 | Miyamoto | |
| 2010/0076267 | A1* | 3/2010 | Sugisawa | A61B 1/0055 600/146 |
| 2011/0046446 | A1 | 2/2011 | Hirayama | |
| 2012/0316394 | A1 | 12/2012 | Yoshida et al. | |
| 2019/0090723 | A1 | 3/2019 | Tanaka et al. | |
| 2020/0305691 | A1* | 10/2020 | Morimoto | A61B 8/12 |

FOREIGN PATENT DOCUMENTS

| | | | | |
|---|---|---|---|---|
| JP | 2007244796 A | * | 9/2007 | A61B 1/00 |
| JP | 5566344 | * | 8/2014 | A61B 1/00 |

OTHER PUBLICATIONS

English Translation via Google of JP5566344 (Year: 2014).*

German Search Report received for DE Application No. 102020111888.0, mailed on Mar. 2, 2021, 13 pages (7 pages of English Translation and 6 pages of Original Document).

International Search Report and Written Opinion received for PCT Patent Application No. PCT/EP2021/061344, mailed on Jul. 23, 2021, 10 pages.

Olympus TJF-Q180V brochure, Jun. 2021, 3 pages.

* cited by examiner

ENDOSCOPE WITH IMPROVED VIEWING WINDOW CLEANING NOZZLE

CROSS REFERENCE TO RELATED APPLICATIONS

This application is a National Stage entry under 35 U.S.C. § 371 of International Application No. PCT/EP2021/061344, filed Apr. 29, 2021, which claims priority from and the benefit of German Patent Application No. DE 10 2020 111 888.0, filed Apr. 30, 2020; said applications are incorporated by reference herein in their entirety.

The present disclosure refers to an endoscope, in particular a single use endoscope, comprising an insertion tube/insertion hose for insertion into a patient's body cavity and a tip at the distal end of the insertion tube/insertion hose, wherein the tip comprises a tip housing encapsulating an optical inspection device for inspecting the patient's body cavity, a viewing window for or of the optical inspection device and a fluid spray nozzle having an outer wall providing a fluid channel surrounded by the outer wall for spraying a fluid onto the viewing window.

BACKGROUND OF THE INVENTION

Endoscopes and similar specialized instruments as bronchoscopes, arthroscopes, colonoscopes, laparoscopes and in particular duodenoscopes are well known from the state of the art and are used for visual examination and diagnosis as well as to assist in surgery. A conventional endoscope generally consists of a connector unit for connecting the endoscope with a supply unit for fluids, gas, light and energy, a control handle connected to the connector unit by a connecting hose/tube and an elongated insertion tube/insertion hose, which on its proximal end (as seen from the operator) is connected to the control handle and on its distal end carries a tip (endoscope tip, duodenoscope tip). In particular in the case of duodenoscopes the tip is an articulating tip, i.e. a tip that can be actively moved and bent into different directions by a respective actuation mechanism and contains several components including illuminating means such as light-emitting diodes or fiber optic light guides connected to a proximal source of light, optical inspection devices as for example image capturing means in form of a miniature video camera, and an elevator for a working instrument like e.g. a forceps elevator.

At this point, the expressions "distal" and "proximal" are defined for the following whole disclosure as follows:

- Distal: In the direction away from a user (toward the patient)
- Proximal: In the direction toward the user (away from the patient)

It is very important that a viewing window in the distal tip casing/tip body, through which the miniature video camera takes images, is clean during use of an endoscope, to provide images from the inside of the body cavity of sufficient and satisfying quality. In particular, dirt, body fluids and organic material adhering or covering the viewing window at least deteriorate the quality of the image, at worst no image can be viewed/taken.

STATE OF THE ART

To avoid or at least reduce problems caused by dirt, body fluids and organic material covering the viewing window it is known in the state of the art to provide the endoscope tip/head with a cleaning nozzle for spraying a cleaning fluid e.g. in form of water onto the viewing window to remove any adhering matter. Such a cleaning nozzle with a straight fluid outlet provided by e.g. a bent metal tube is known for example from U.S. Pat. No. 6,595,915 B2, which discloses a jet nozzle connected to a distal end of an axial wash fluid passage in an endoscopic insertion instrument for spurting a wash fluid toward and on an observation window of an optical image pickup system fitted in a tip end section of said endoscopic insertion instrument, said jet nozzle comprising a wash fluid inlet passage provided in an axial bore formed axially through said tip end section in a direction of an optical axis of said optical image pickup system and opened in a circular end face of said tip end section; and a nozzle tip portion having a jet spout passage portion and a curved turn passage portion, wherein said jet spout passage portion is extending along a distal end face of said tip end section and provided with a flat flow rectifying passage; and said curved turn passage portion is connecting said wash fluid inlet passage and said jet spout passage portion to turn a flow passage of said wash fluid from said axial wash fluid passage to said jet spout passage portion and is bent such that a center line of said flow rectifying passage is brought into alignment with a center of said observation window.

One drawback of such cleaning nozzles is that the fluid flow exiting the cleaning nozzle widens/expands after leaving the nozzle, such that the result of cleaning is less satisfying. To provide better cleaning results, a use of guiding elements provided on side walls of a cleaning nozzle is known. Such guiding elements provide a split pathway for fluid giving a certain direction to the flow. However, after leaving the nozzle and the area of guiding elements, the flow of fluid regularly widens/diverges/deconcentrates which results in an unfavorable degradation of cleaning effect.

For example, U.S. Pat. No. 6,409,657 B1 discloses a medical endoscope having an insertion section including a distal viewing head which is connected to an operating section through a flexible section and includes an illumination system located behind an illumination window, a viewing lens system located behind a viewing window, fluid feed means for feeding at least cleaning fluid to the viewing window, and suction feed means for feeding suction to the viewing head, said medical endoscope comprising a generally cylindrical viewing head casing for housing said illumination system, said viewing lens system and said fluid feed means therein, a generally annular-shaped viewing head cap detachably fitted to said generally cylindrical viewing head casing, said viewing head cap being formed so as to have a generally cylindrical wall extending a predetermined height from a distal end of said viewing head casing in a lengthwise direction of said insertion section, a fluid feeding nozzle having a fluid injection port through which said cleaning fluid can be fed, said fluid feeding nozzle being formed integrally with said generally annular-shaped viewing head cap and configured to form a fluid path which is brought into communication with said fluid feed means when said generally annular-shaped viewing head cap is fitted to said generally cylindrical viewing head casing and is turned to direct said cleaning fluid through said fluid feed means toward said viewing window, and a drain path opening to a space formed between said cylindrical wall of said generally annular-shaped viewing head cap and said distal end of said viewing head at a distal end and being in communication with said suction feed means at a proximal end so that liquid that stays in said space is sucked through said drain path into said suction feed means. Additionally, there is provided an air blowing port, for blowing air onto the viewing window after washing it with rinsing water by the fluid feeding nozzle. The fluid feeding nozzle as well as the air feeding nozzle are arranged angularly to each other and are both concentrated on the viewing window.

U.S. Pat. No. 8,591,406 B2 discloses an endoscope comprising an observation port that is provided at a distal end of said endoscope and collects light reflected from an object, a fluid supply pipe that transmits gas and/or liquid to a distal end thereof, a cap that blocks the distal end of said fluid supply pipe and is configured so that a partially enclosed semispherical space is created between the distal end of said fluid supply pipe and an inner surface of said cap, a fluid ejection channel that has an outlet facing said observation port, and extends from an edge of an opening at the distal end of said fluid supply pipe to the outlet and occupies the semispherical space inside said cap, and a direction adjustment protrusion that extends over the outlet in a lengthwise direction of said fluid ejection channel, wherein when the outlet faces said observation port, a plane of projection projecting toward said observation port is parallel to the outlet and a lengthwise direction of the plane of projection is parallel to a circumferential direction of the outlet, said direction adjustment protrusion is configured at a center of said outlet in the circumferential direction, and a downward projected length of said direction adjustment protrusion continuously increases in the lengthwise direction of said fluid ejection channel toward the outlet, such that said direction adjustment protrusion extends toward a center of the fluid ejection channel. The projection results in a widening/splitting of the fluid flow coming out of the nozzle, such that a wide cleaning area can be provided by a small fluid nozzle.

SUMMARY OF THE INVENTION

Against this background, the object of the present disclosure is to reduce the mentioned disadvantages of the prior art, and in particular to provide an endoscope with a viewing window, which is better, easily and efficiently to clean.

This object is achieved by an endoscope according to claim 1, i.e. an endoscope, in particular single use endoscope/duodenoscope comprising an (flexible) insertion tube/endoscope shaft for insertion into a patient's body cavity and a tip/endoscope head at the distal end/end portion of the insertion tube, which tip/endoscope head is optionally connected with the (flexible) insertion tube via a so-called deflecting being actively/manually bendable by an actuation mechanism provided at/in a control handle connected with a proximal end of the insertion tube, wherein the tip comprises a tip housing/casing/body encapsulating an optical inspection device (video/photo camera and optionally lens system) for inspecting the patient's body cavity, a viewing window connected to/integrated with the tip housing for or of the optical inspection device and a fluid/liquid spray nozzle provided by or mounted at the tip housing which fluid spray nozzle has an outer wall (nozzle casing) providing/forming at least a fluid/liquid channel surrounded by the outer wall for feeding and spraying a (cleaning/rinsing) fluid/liquid onto the viewing window, the fluid/liquid channel having a flattened or slit-like cross section, in particular an elongated oval cross section, so that a height of the cross section in a height direction is smaller than a width of the cross section in a lateral direction, wherein the fluid/liquid spray nozzle, especially the fluid/liquid channel comprises at least one fluid/liquid splitting element arranged in the fluid/liquid spray nozzle, especially the fluid/liquid channel, the fluid/liquid splitting element splitting the fluid channel into a first lateral channel on a first side in the lateral direction of the fluid/liquid splitting element and into a second lateral channel on a second side in the lateral direction of the fluid/liquid splitting element, said splitting element is designed/shaped to provide a converging fluid/liquid flow (flow constriction) out of the nozzle (downstream the nozzle) onto the viewing window. Preferably exactly one fluid/liquid splitting element is provided splitting the fluid/liquid channel into exactly two channels, namely the first lateral channel and the second lateral channel.

The endoscope according to the disclosure in particular is very well suited for a use in the gastrointestinal area, i.e. as a duodenoscope. As the fluid/liquid flow coming out of the fluid/liquid spray nozzle converges when/after leaving the nozzle based on the effect of the splitting element, a very efficient cleaning can be provided, as essentially the entire fluid/liquid can be accurately targeted onto the viewing window to be cleaned. Therefore, a very good cleaning effect can be achieved with a relatively small amount of fluid/liquid. With other words, one can say that the disclosure provides an (single-use) endoscope/duodenoscope with a fluid/liquid spray nozzle having a split fluid/liquid channel/split fluid/liquid path way for concentrating/converging/tapering the spray outlet, or more concrete the fluid/liquid outlet to the viewing window.

The optical inspection device of the endoscope in particular may comprise an imaging system/imaging device like a camera, for example an imaging chip or a CCD camera, in particular for taking pictures and/or film sequences. Further, the optical inspection device may comprise a focusing/lens system for focusing an image on the camera. Such focusing system may be in form of a lens, a lens system, a lens stack, etc. In particular it may be an adjustable focusing system. The viewing window may be a protective light transparent (glass) plate, preferably a plane-parallel plate or a focusing lens, which each may form part of the focusing system. In particular, the tip housing may encapsulate the optical inspection device in a fluid tight manner. The lens system may be in the form of a lens barrel which partly penetrates the tip housing provided with a respective through hole. It may in particular be an adjustable lens system for varying the position of focus. The optical axis of the lens system may be oriented in an angle of 4° to 10° to the vertical of a longitudinal axis of the tip housing, most preferred of 6° to the vertical of the longitudinal axis, such that the viewing direction of the tip is a little bit to the backside/to the proximal direction.

The tip according to the disclosure provides a kind of a camera tip for an endoscope as well as for a duodenoscope. The tip housing in particular may be made of a plastic/resin material. Such a material could be any transparent material, however, it is preferred to use a transparent plastic material. Plastic material has a number of advantages for a single use tip, as e.g. low cost, adequate mechanical characteristics as elasticity, low brittleness, a high suitability for manufacturing methods as injection molding and light weight. Light emitted from the light emitting device can easily penetrate through the transparent material of the tip housing and may be sent to the outside, e.g. into a body cavity, from at least a part of the outer surface of the housing. The tip housing in particular may be made by injection molding of a transparent plastic material. It may therefore be made with a nearly unlimited geometry and required dimensions. Additionally, injection molding is well suited for making a high number of parts with low costs. According to the invention the housing may be monolithically made from the transparent material and provide a one-part-tip. This is advantageous as no sealing is required between distinct parts. However, the housing may be designed as a multi-part housing.

In the description of the present disclosure and its preferred embodiments/examples reference is made to the following terms of direction/location:

The direction between distal and proximal is referred to as the longitudinal direction.

A longitudinal axis is arranged in the longitudinal direction in the middle of the tip.

A direction which is orthogonal to a plane comprising the longitudinal direction and the viewing direction of the optical inspection device is referred to as the lateral direction.

Finally, a direction orthogonal to the longitudinal direction as well as to the lateral direction is referred to as the height direction.

Advantageous embodiments of the invention are claimed in the dependent claims and are explained in more detail below.

According to one (independent) embodiment, the fluid/liquid spray nozzle has a flattened or slit-like cross section, in particular flattened in the height direction. The fluid/liquid spray nozzle in particular may have an elongated oval cross section, in particular elongated in the width direction. The height of the cross section in height direction (essentially perpendicular, or more concrete 90°-α, as described below) to the optical axis of the optical inspection device) in particular may be in a range between 0.1 mm to 1 mm, preferably between 0.2 mm and 0.5 mm, more preferred of 0.3 mm. Such a height advantageously provides a flat fluid/liquid stream the direction of which in height axis is clearly defined. Additionally or alternatively, a width of the cross section in the width direction (essentially parallel (0°-α) to the plane of the viewing window) may be in the range between 0.5 mm to 3 mm, preferably between 1 mm and 2.5 mm, more preferred of 1.5 mm to 2 mm. Such a width provides sufficient space/width for providing the fluid/liquid splitting element in the fluid/liquid spray nozzle, especially in the fluid/liquid flow channel and for converging the fluid/liquid stream extending the fluid/liquid spray nozzle, especially the fluid/liquid channel. The terms height and width refer to dimensions of the fluid/liquid spray nozzle (and also the fluid/liquid channel of the nozzle) essentially perpendicular to the longitudinal axis of the endoscope tip, i.e. to dimensions in the height direction and the width direction, respectively. The longitudinal axis of the tip/the tip housing extends in the direction from proximal to distal (from a proximal end of the housing to a distal end of the housing).

A further (independent) embodiment is characterized in that the at least one fluid/liquid splitting element is arranged essentially in the crossectional center of/in the fluid/liquid channel itself, in particular essentially in the crossectional center with regard to the width of the fluid/liquid channel. This advantageously results in the fluid/liquid flow exiting the nozzle/the flow channel being converged in a direction parallel to the plane of the viewing window. Preferably, the cross section of the at least one fluid/liquid splitting element is constant in height direction. This allows to converge the fluid/liquid stream exiting the fluid/liquid channel (and therefore the fluid/liquid spray nozzle) in the width direction, but to keep the stream unchanged in the height direction, and to, therefore, focus the stream very exactly onto the viewing window.

The fluid/liquid splitting element may extend over an entire height of the fluid/liquid channel in the section of the fluid/liquid channel where the fluid/liquid splitting element is arranged. In particular, the fluid/liquid splitting element may be connected to/ may connect two opposed portions of the outer wall forming the fluid/liquid channel.

According to a further (independent) embodiment, the at least one fluid/liquid splitting element on its outflow side/proximal side comprises a sharp edge, which preferably is located within the fluid path/the fluid/liquid channel surrounded by the outer wall or right at the outflow end of the fluid path/the fluid/liquid channel surrounded by the outer wall. A fluid splitting element with a downstream-side sharp edge allows a very effective converging of the fluid/liquid stream, as the pressure in the fluid flow significantly drops at the sharp edge, thereby forging the fluid towards the middle of the fluid stream.

A further (independent) embodiment is characterized in that the at least one fluid/liquid splitting element has a prism/wedge like shape with a triangular base plane (when seen form above), in particular two triangular base planes, one at its top and one at its bottom (when viewed in height direction/when seen from above or below). The base plane preferably is arranged essentially parallel to the direction of fluid/liquid flow, i.e. parallel to the longitudinal direction and/or the width direction. Further, a vertex of the base plane preferably is arranged on the inflow side/proximal side (upstream side) and a rectangular plane opposite said vertex being arranged on the outflow side/distal side (downstream side). The fluid/liquid splitting element in one embodiment may have a prism/wedge like shape with two isosceles triangular base planes. In particular, the triangular base planes may have convex shaped side planes. Preferably, the distal end/distal plane of the fluid/liquid splitting element is arranged on a level with the distal end of the fluid/liquid channel. Alternatively, the distal end/distal plane of the fluid/liquid splitting element is arranged in flow direction proximal (upstream) the distal end of the fluid/liquid spray nozzle and preferably proximal (upstream) the distal end of the fluid/liquid channel. Preferably, the cross section of the fluid/liquid splitting element is constant in height direction.

One preferred (independent) embodiment is characterized in that the viewing window/the protective plate is/are inclined towards the fluid/liquid spray nozzle. The inclination of the outer surface of the viewing window/protective plate relative to the longitudinal axis of the tip, i.e. relative to a plane comprising the longitudinal direction as well as the width direction, in particular may be at an angle α of 4° to 10°, preferably of 6°. Such an inclination of the surface to be cleaned allows a very effective interaction with the fluid stream used for cleaning.

Further, as another (independent) embodiment, the fluid/liquid spray nozzle may comprise an (additional) gas/air channel, in particular for an inert gas or air. This additional gas channel may be arranged laterally beside (parallel to) the fluid/liquid channel (in a fluid-separate manner) within the spray nozzle (element). Preferably, the gas channel is arranged parallel to the fluid channel.

The fluid/liquid spray nozzle in particular may comprise a first inlet on its proximal side for rinsing fluid and a second inlet on its proximal side for the additional gas. The fluid/liquid channel and the additional gas channel being provided inside the fluid/liquid spray nozzle and being connected to the first and second inlets, respectively, each have a distal outlet for fluid and gas, respectively, which may be arranged preferably immediately adjacent (parallel/besides) to each other. The inlets and outlets of the nozzle are fluidically connected to concerning fluid conduits/fluid lines provided in the bending element and the insertion tube/hose.

Advantageously, the distal outlets of the fluid channel and the additional gas channel open into a mixing chamber/area/depression at/in the distal end portion of the fluid/liquid spray nozzle, which mixing chamber is distally open in the direction to the viewing window to be cleaned. The mixing chamber may be formed by the fluid/liquid spray nozzle, in particular the nozzle housing and/or the outer walls of the fluid/liquid channel and/or the gas channel, or by a part of the nozzle and a part of the tip housing. The additional gas channel allows a supply of gas, for example of $CO_2$ and water. Such gas can be mixed with the fluid/liquid supplied by the fluid channel, in particular in the mixing chamber, which mixing lowers the viscosity of the fluid/liquid and hence increases the flow. Additionally, such mixing also provides a (more) turbulent flow resulting in an improved capability of cleaning the viewing window.

The fluid/liquid spray nozzle in particular may be made (exclusively) from plastic/resin, in particular by injection molding. The fluid spray nozzle can be made of a transparent material, e.g. a transparent plastic/resin material. Preferably, the fluid spray nozzle may be connected to the housing by a transparent adhesive or a transparent glue or by a transparent grout. By using a transparent nozzle material and a transparent grout, respectively, formation of shadows and drop shadows can easily and effectively be avoided, which results in high image quality. Also, the fluid spray nozzle and the tip housing may be monolithically formed, in particular from a plastic material or a transparent plastic material.

In summary, it can be said that the disclosure in particular may provide the following features and/or advantages:

- gas/air and fluid/water flow in separate tubes/channels in the endoscope, in particular in the insertion tube/hose and the bending part/element
- they are connected to the spray nozzle, which provides different/separate inlets for gas/air and fluid/water
- the mixing chamber is provided by the spray nozzle, in particular by the spray nozzle housing, and the tip housing
- exclusively the rinsing fluid/water is blocked/split by the fluid/liquid splitting element in front of the viewing window/protective plate/lens system (in flow direction upstream), which means at the outlet of the fluid/liquid channel into the mixing chamber
- after passing the fluid/liquid splitting element fluid/water is allowed to flow back towards the middle and to concentrate on the viewing window/protective plate/lens system
- flushing of the viewing window/protective plate/lens system is amplified by the converged fluid/liquid flow
- the fluid/liquid splitting element may have any suitable geometry, in particular it may have a round, oval, triangular or isosceles triangular cross section in particular in a plane comprising the longitudinal direction and the width direction
- the tip is very well suited for single use and is intended to be discarded after use
- the tip is provided with excellent cleaning capability due to converging the flow of cleaning fluid onto the viewing window

SHORT DESCRIPTION OF THE FIGURES

Figure 2:
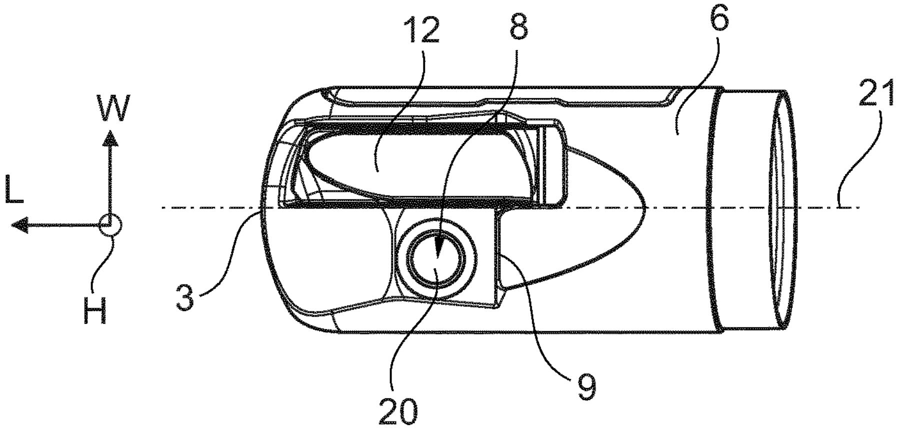
Figure 3:
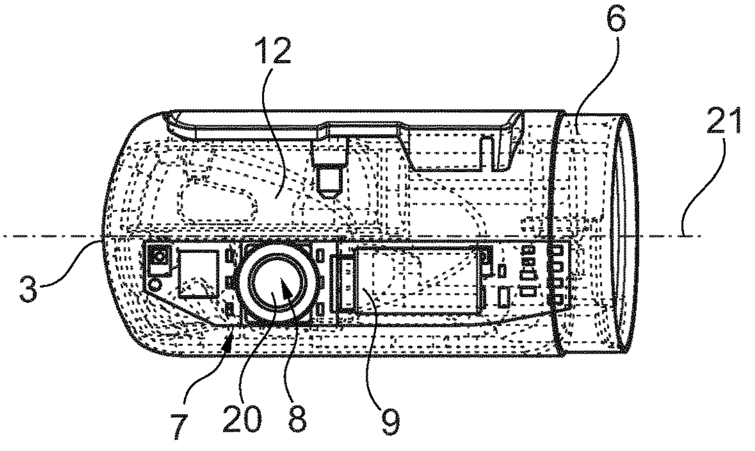
Figure 4:
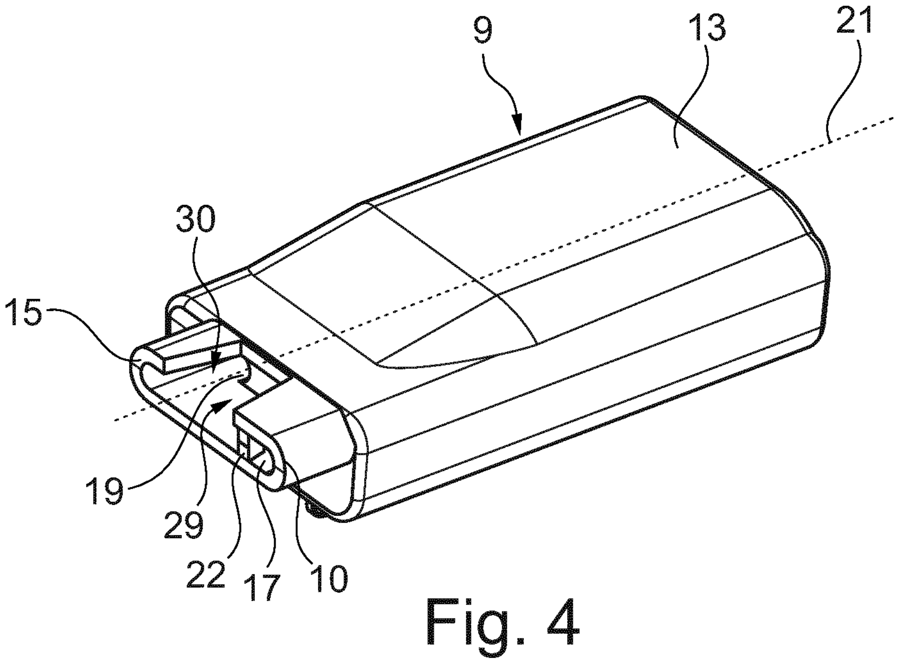
Figure 5:
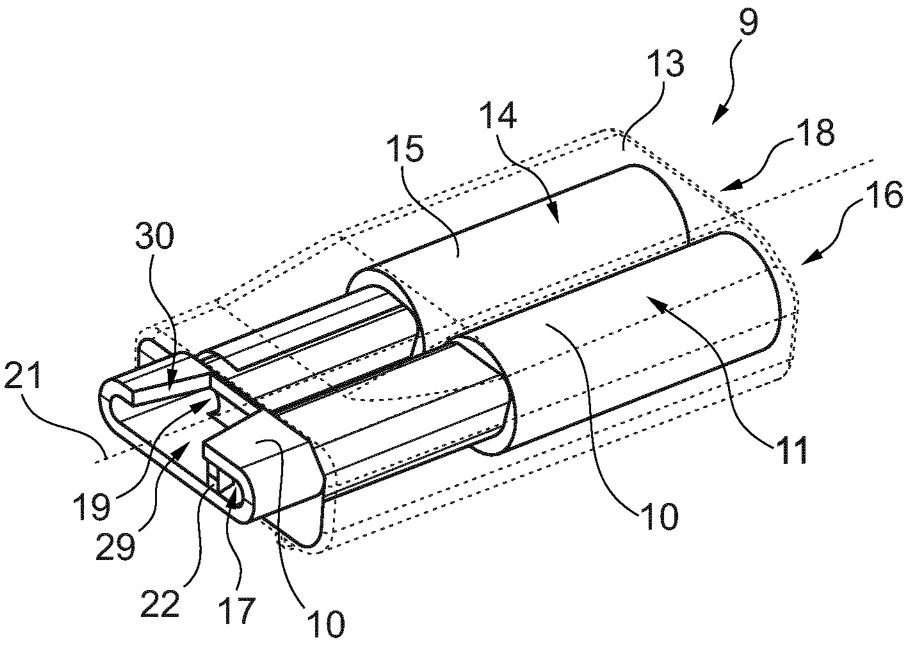
Figure 6:
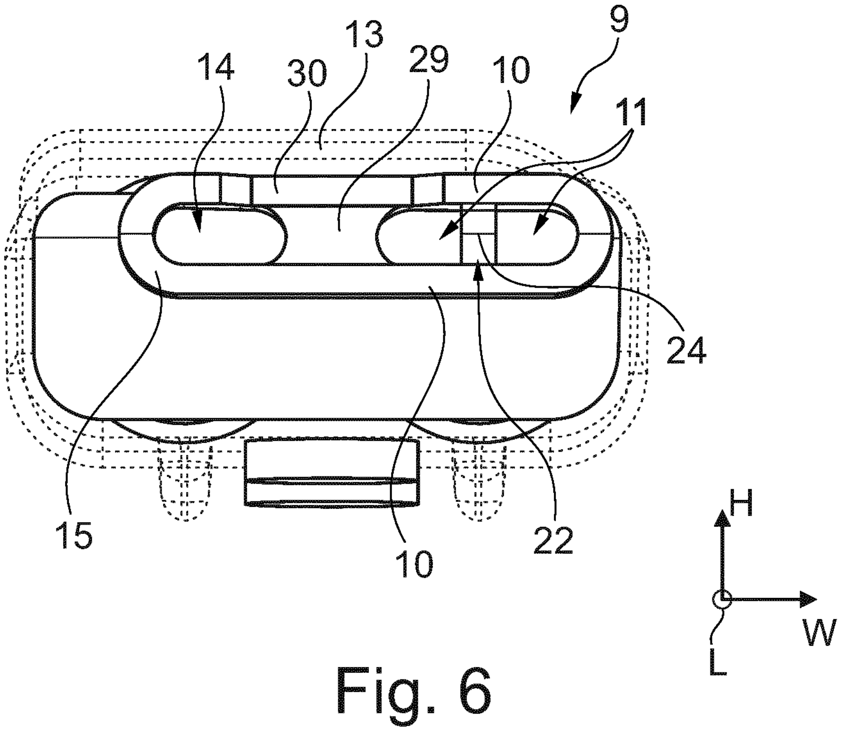
Figure 7:
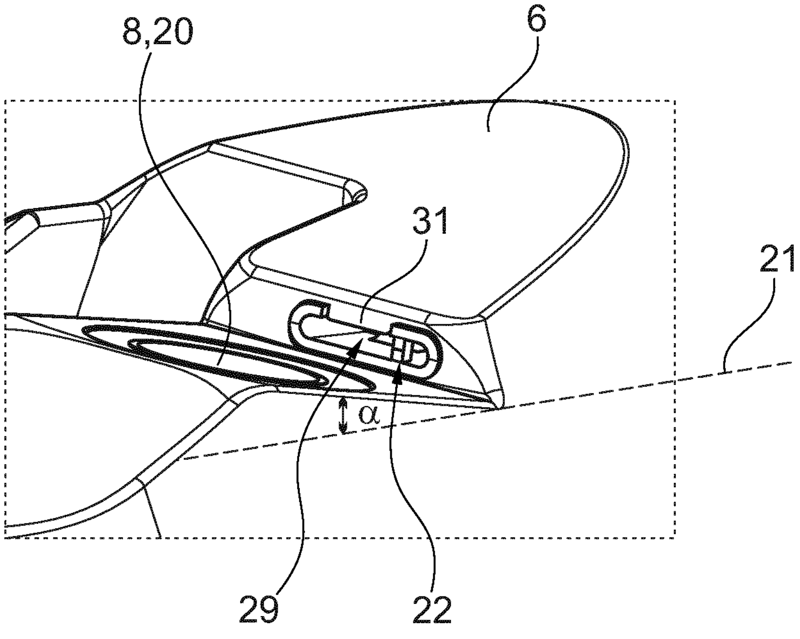
Figure 8:
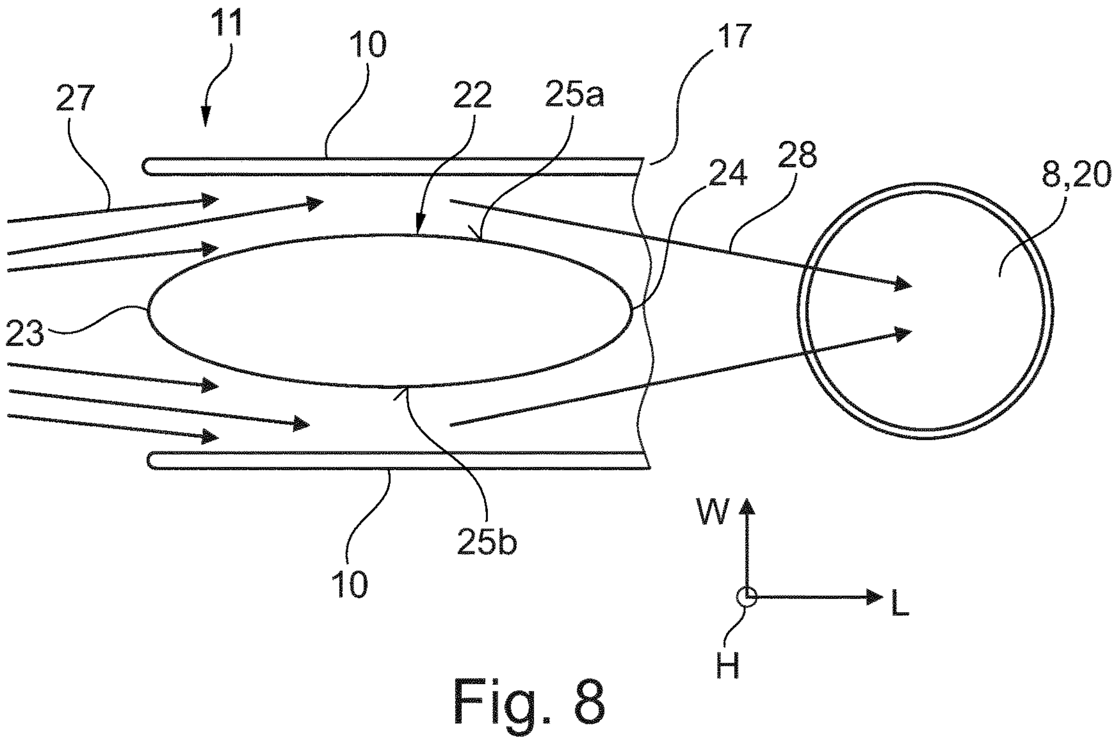
Figure 9:
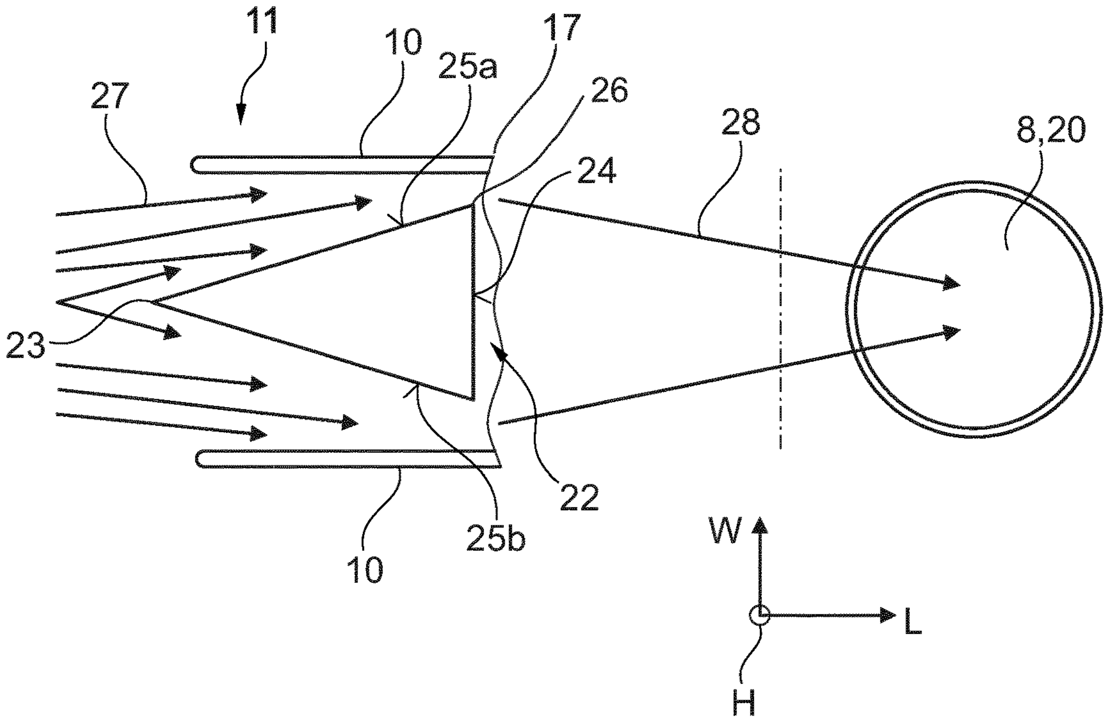
Figure 10:
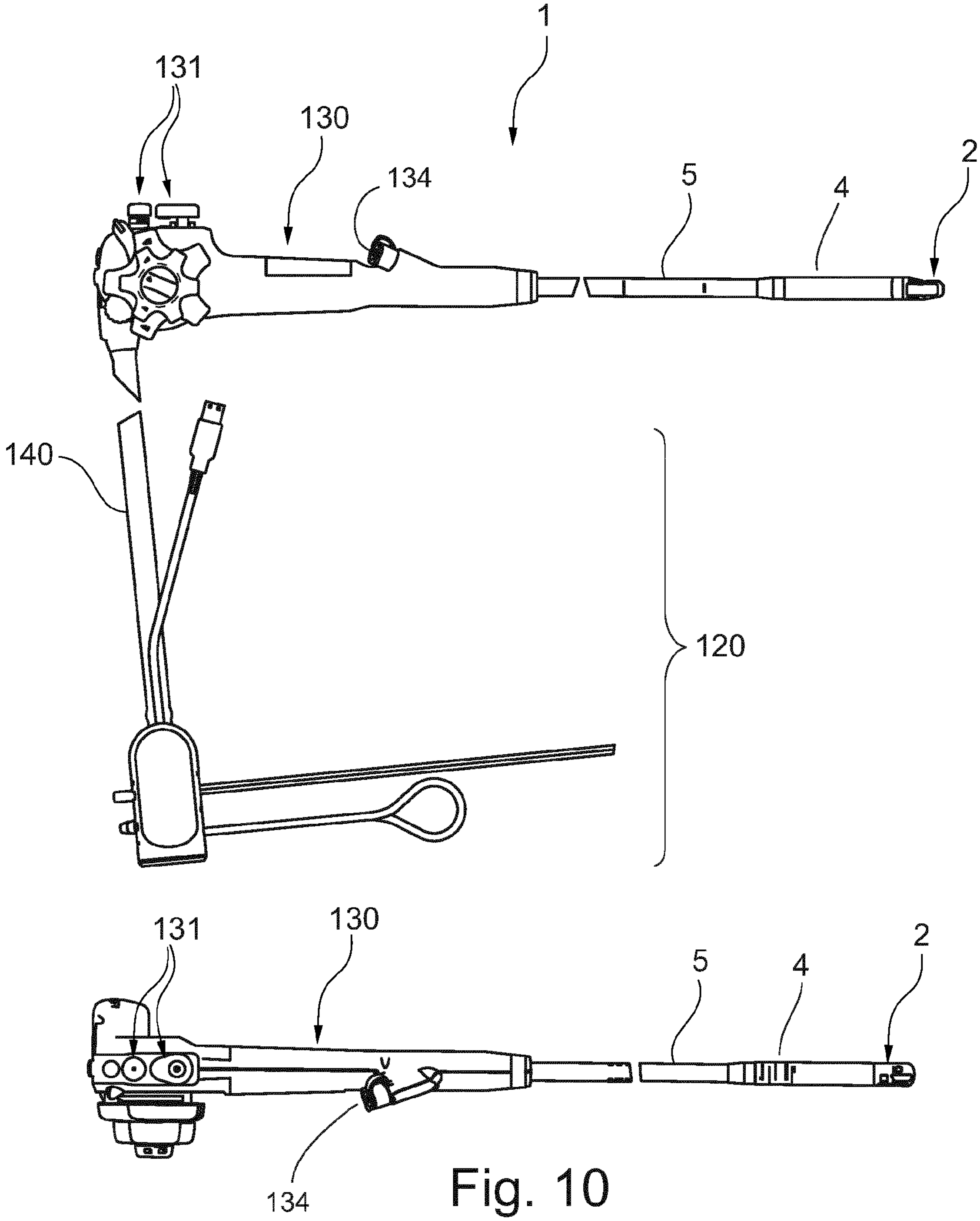

Further features and advantages of the present disclosure result from the following exemplary and non-limiting description of the figures. These are only schematic in nature and only serve to understand the disclosure:

FIG. 1 shows a perspective partial view of an example of an endoscope insertion hose with a distal tip according to the disclosure, FIG. 2 shows a plan view on the tip of the endoscope of FIG. 1, FIG. 3 shows plan view on the tip of the endoscope of FIG. 1 having a transparent tip housing, FIG. 4 shows a perspective view of one embodiment of a fluid nozzle of an endoscope of the disclosure, FIG. 5 shows a perspective view of another embodiment of a fluid nozzle of an endoscope of the disclosure, FIG. 6 shows a plan view of the fluid nozzle taken from proximal to distal, FIG. 7 shows a perspective view of a part of the tip of an endoscope of the disclosure, FIG. 8 shows a schematic diagram of a sectional top view of the fluid channel taken along the longitudinal axis from distal to proximal, FIG. 9 shows a schematic diagram of a sectional top view of the fluid channel taken along the longitudinal axis from distal to proximal in another embodiment and FIG. 10 shows an endoscope/duodenoscope according to the present disclosure.

DESCRIPTION OF THE PREFERRED EMBODIMENTS

To begin with, FIG. 10 shows the endoscope 1 of the present disclosure in its substantially complete structure.

Accordingly, the endoscope 1 is preferably a single use endoscope (duodenoscope) and comprises a connector unit 120 for connecting the endoscope 1 with a (separate) supply unit, which may also be referred to as a base unit, for at least one operating resource (for example, electric power, water, etc.). The endoscope 1 further comprises a supply line 140 located proximal (in the direction toward the user) to/at the connector unit. The supply line 140 is for supplying said at least one operating resource from the connector unit 120 to an endoscope handle 130 which is designed to be held by a user and—in accordance with the manual actuations of several manipulators 131 at the handle 130 by the user—from the handle 130 to a distal (direction away from the user/direction toward the patient) endoscope tip/head 2 (shown in FIG. 1), which is intended to be inserted into a patient's body cavity and which is located at the distal end of an endoscope shaft 5 which shaft 5 is mounted at its proximal end to the handle 130 and into which the supply line is extended. Furthermore, the endoscope shaft 5 comprises at least one so-called working channel 134 extending along the endoscope shaft 5 and having an opening in the tip 2 such that a surgical instrument can be shifted through the working channel 134 to extend beyond the tip 2 into a distal and/or radial direction.

In the following, the direction of height (H), width (W) and length/longitudinal axis (L) are partly indicated in the figures (see longitudinal axis 21). FIG. 1 shows a perspective view of a distal end area of the endoscope 1/duodenoscope 1 according to one example of the disclosure. The endoscope 1 is, as already stated above, a single use endoscope 1, for example a single use duodenoscope 1, intended to be discarded after use and comprises the tip 2 arranged at a distal end 3 of a bending part (deflecting) 4 of the endoscope shaft/insertion tube 5 (insertion hose 5) indicated in FIG. 1 by dashed lines. The proximal end of the bending part 4 is connected to/arranged on the distal end of the insertion tube 5. The entity composed of the tip 2, the bending part 4 and the insertion tube 5 is intended for insertion into a patient's body cavity. By manually bending the bending part 4 in a well-known manner in the lateral direction and/or the height direction the orientation in space of the tip 2 can be changed.

The tip 2 comprises a tip housing 6 encapsulating an optical inspection device 7 for inspecting the patient's body cavity. The tip 2 further comprises a viewing window 8, which forms a functional part of the optical inspection device 7, and a fluid/liquid spray nozzle 9 having an outer wall 10 providing a fluid/liquid channel 11 surrounded by the outer wall 10 for spraying a fluid/liquid onto the viewing window 8. The tip housing 6 of the example shown in FIGS. 1 and 2 is made from injection molding of an opaque plastic/resin material. The tip housing 6 of the example shown in FIG. 3 is made from injection molding of a transparent plastic/resin material. Laterally adjacent the viewing window 8 there is preferably an albarran lever 12, which is well known as such and not further described herein.

The fluid/liquid spray nozzle 9, examples of which are shown in FIGS. 4 and 5, is inserted into a cavity of the tip housing 6. The fluid/liquid spray nozzle 9 comprises a nozzle housing 13, which is inserted into the tip housing 6 from distal to proximal and held therein by engagement with the tip housing 6. A longitudinal axis of the fluid/liquid nozzle 9 is substantially parallel to the longitudinal axis 21 of the tip 6/endoscope 1. Inside the nozzle housing 13 the fluid/liquid spray nozzle 9 comprises the fluid/liquid channel 11 surrounded by the outer wall 10 and an additional gas channel 14 surrounded by a further outer wall 15 (which is also part of the nozzle housing 13). The gas channel 14 is arranged laterally adjacent the fluid/liquid channel 11. The fluid/liquid channel 11 comprises a proximal inlet opening 16 and a distal outlet opening 17. The gas channel 14 comprises a proximal gas inlet opening 18 and a distal gas outlet opening 19. Both channels 11, 14 essentially extend in the longitudinal direction and are formed monolithically.

As shown in particular in FIG. 6, the outlet opening 17 of the fluid/liquid channel 11 is designed in form of a slit. The outlet opening 17 has a flattened or slit-like cross section, here an oval cross section, elongated in the lateral direction (W). The height of the cross section/outlet opening 17 according to the invention is in the range between 0.1 mm to 1 mm, in the example shown 0.3 mm. The width of the cross section/outlet opening 17 in the lateral direction according to the invention is in the range between 0.5 mm to 3 mm, here 1.5 mm. This geometry of the outlet opening 17 provides a stream of fluid with a flat shape, i.e. a certain width and a much smaller height.

As especially shown in FIGS. 1 and 7, the viewing window 8 is inclined with respect to the longitudinal axis 21 extending from distal to proximal of the tip 6. The viewing window 8 is further closed by/comprises a protective glass plate 20, here in form of a plane-parallel plate 20. Alternatively, the viewing window 8 is closed by/comprises a focusing lens, which each may form part of a focusing system (not shown in the figures) forming part of the optical inspection device 7. In particular, the viewing window 8 is inclined relative to the longitudinal axis 21 of the fluid spray nozzle 9/of the tip 6 towards the proximal direction by an angle $\alpha$ of 4° to 10°, preferably of 6°, while the fluid/liquid channel 11 and the gas channel 14 both are essentially parallel to the longitudinal axis 21. This means that the optical axis is inclined at the angle a towards the height direction (H).

At the distal outlet opening 17 of the fluid channel 11 there is arranged a fluid/liquid splitting element 22. Preferably, the fluid/liquid splitting element 22 is located at the distal end of the fluid channel 11. The aim of the fluid/liquid splitting element 22 is to provide a converging fluid/liquid flow out of the nozzle 9 onto the viewing window 8, i.e. forming the flat shaped stream of fluid into a converging flat stream of fluid. The fluid stream converges in width direction (W). The fluid splitting element 22 is arranged essentially in the crossectional center with regard to the width of in the fluid channel 11. It provides a barrier/resistance having a hydraulic impact on the fluid flowing through the fluid channel 11. The fluid splitting element 22 splits the fluid channel 11 into a first lateral channel and a second lateral channel, as can be in particular seen in FIG. 6. The fluid splitting element 22 extends over an entire height of the fluid channel 11 so that the fluid splitting element 22 is connected to two opposed portions of the outer wall 10 forming the fluid channel 11.

As in particular shown in the top sectional view of FIG. 9 taken in width direction and showing a cross section in a plane parallel to the longitudinal direction, the fluid splitting element 22 comprises a proximal pointed or tip-like end/edge 23, which in the direction of flow is an upstream end/edge 23, and a distal flat end/surface 24, which in the direction of flow is a downstream end/surface 24. Between the proximal end/edge 23 and the distal end/surface 24 the fluid splitting element 22 comprises lateral surfaces **25*a*, 25*b* providing a guiding effect on fluid flowing through the fluid channel 11 and past the fluid/liquid splitting element 22. FIG. 8 shows a different fluid/liquid splitting element 22 having an essentially oval or lens-like form with its proximal end 23 and its distal end 24 each being formed as a rounded tip/edge. The lateral surfaces 25 a, 25*b* as well as the distal ends/edges 24 are arcuate. The form of the cross section of the fluid/liquid splitting elements 22 of FIGS. 8 and 9** is constant in height direction.

The fluid/liquid splitting element 22 provides a narrowing/restriction of the flow cross section. FIG. 9 shows an advantageous form of the fluid/liquid splitting element 22, which on its outflow side 24 comprises sharp edges 26 formed by the surface 24 and the concerning lateral surfaces **25*a*, 25*b*. The sharp edges 26 are both located right at the outflow end of the fluid/liquid path 11 surrounded by the outer wall 10. The fluid/liquid splitting element 22 shown in FIG. 9 therefore has a prism like shape with a triangular base plane 32 shown as a triangle in FIG. 9, in particular with an isosceles triangular base plane. The base plane 32 is arranged essentially parallel to the direction of fluid flow, i.e. parallel to the longitudinal direction. The vertex 23 of the base plane 32 is arranged on the inflow side and the distal surface 24 in form of a rectangular plane is arranged opposite said proximal vertex 23 on the outflow side. Such a geometry is very efficient for providing the desired converging effect on the outflowing fluid and provides a nozzle 9** of very short length.

FIGS. 8 and 9 each show the fluid flow in the fluid/liquid channel 11 by arrows 27 as well as the fluid flow outside the fluid channel 11 by arrows 28. The converging flow outside the fluid channel 11 is focused onto the viewing window 8 and is clearly shown.

As especially shown in FIGS. 4, 5, 6 and 7 on the outflow side/downstream of the fluid channel 11 and the gas channel 14 there is provided a mixing chamber 29, which partly is delimited by the outer wall 10. At the top of the mixing chamber 29, there is preferably formed a recess 30. When installed in the tip housing 6, a protrusion 31 provided at the tip housing 6 engages with the recess 30 and thus also forms part of the wall of the mixing chamber 29. By the engagement of the recess 30 and the protrusion 31 the nozzle 9 easily can be aligned with regard to the viewing window 8.

As stated above, the fluid/liquid splitting element 22 does preferably not (or only partly) extend into the mixing chamber 29 into which the fluid/liquid channel 11 and the gas channel 14 opens, respectively. Accordingly, a mixing effect of the liquid and the gas is achieved which mixture is substantially concentrated/focused to the viewing window by the converging effect of the splitting element 22 inside the opening of the fluid/liquid channel 11.

REFERENCE SIGNS

1 endoscope
2 tip, endoscope tip
3 proximal end
4 bending part
5 insertion tube, insertion hose
6 tip housing
7 optical inspection device
8 viewing window
9 fluid spray nozzle
10 outer wall
11 fluid channel
12 albarran lever
13 nozzle housing
14 gas channel
15 outer wall
16 distal inlet opening
17 proximal outlet opening
18 distal gas inlet opening
19 proximal gas outlet opening
20 protective glass plate, plane-parallel plate
21 longitudinal axis
22 fluid splitting element
23 distal pointed end/edge, distal tip-like end/edge
24 proximal flat end, proximal surface
25*a,b* lateral surface
26 sharp edge
27 arrows indicating fluid flow
28 arrows indicating fluid flow
29 mixing chamber
30 recess
31 protrusion
32 base plane
120 connecting unit
130 control handle
131 manipulators
134 working channel
140 supply line

What is claimed is:

1. An endoscope comprising:
an insertion tube; and
a tip at a distal end of the insertion tube, the tip including:
an optical inspection device;
a viewing window for or of the optical inspection device;
a tip housing encapsulating the optical inspection device; and
a fluid spray nozzle comprising:
an outer wall providing a fluid channel surrounded by the outer wall for spraying a fluid onto the viewing window, the fluid channel having a transverse cross-section having a height (H) and a width (W), the height being smaller than the width and defining a height direction, the width defining a lateral direction; and
a fluid splitting element arranged in the fluid channel and having a first side and a second side opposite the first side in the lateral direction, the fluid splitting element splitting the fluid channel into a first lateral channel and a second lateral channel, the first lateral channel located on the first side of the fluid splitting element and the second lateral channel located on the second side of the fluid splitting element, the fluid splitting element comprising a vortex, a first lateral surface forming part of the first lateral channel, a second lateral surface forming part of the second lateral channel, and a maximum width extending from the first lateral surface to the second lateral surface and being distal of the vortex, the fluid splitting element being configured to increasingly compress flow along a longitudinal direction from the vortex to the maximum width through the first lateral channel and through the second lateral channel and to thus provide a converging fluid flow out of the fluid spray nozzle onto the viewing window,
wherein the fluid spray nozzle is positioned in the tip housing longitudinally adjacent and proximally of the viewing window, and
wherein the viewing window is inclined toward the fluid spray nozzle on a plane intersecting a plane of the fluid spray nozzle, the plane of the fluid spray nozzle being parallel to the longitudinal direction and extending along the lateral direction.

2. The endoscope of claim 1, further comprising an Albarran lever positioned in the tip housing laterally adjacent to the fluid spray nozzle.

3. The endoscope of claim 1, wherein the viewing window is inclined towards the fluid spray nozzle at an angle of 4° to 10° relative to the height direction.

4. The endoscope of claim 1, wherein a longitudinal cross-section of the fluid channel comprises an elongated oval shape having a major axis and a minor axis, and wherein a transverse plane encompassing the minor axis encompasses the maximum width.

5. The endoscope of claim 1, wherein the height of the transverse cross-section is in the range between 0.1 mm to 1 mm and/or the width of the cross-section is in the range between 0.5 mm to 3 mm.

6. The endoscope of claim 5, wherein the height of the transverse cross-section is in the range between 0.2 mm and 0.5 mm.

7. The endoscope of claim 5, wherein the width of the transverse cross-section is in the range between 1 mm and 2.5 mm.

8. The endoscope of claim 7, wherein the width of the transverse cross-section is in the range between 1.5 mm and 2 mm.

9. The endoscope of claim 1, wherein the fluid splitting element is arranged in a cross-sectional center of the fluid channel.

10. The endoscope of claim 1, wherein the fluid splitting element has a proximal end opposite a distal end in the longitudinal direction, a width of a longitudinal cross-section varying in the longitudinal direction.

11. The endoscope of claim 10, wherein the maximum width of the transverse cross-section is intermediate the proximal end and the distal end of the fluid splitting element.

12. The endoscope of claim 10, wherein the fluid splitting element has a prism like shape with a triangular base plane comprising the vertex and a rectangular surface extending vertically at the distal end of the fluid splitting element.

13. The endoscope of claim 12, wherein the prism like shape includes the first lateral surface, connecting the vertex to the rectangular surface, and the second lateral surface, connecting the vertex to the rectangular surface, a sharp edge being formed at a junction of the first lateral surface and the rectangular surface and a sharp edge being formed at a junction of the second lateral surface and the rectangular surface.

14. The endoscope of claim 13, wherein the rectangular surface is located within the fluid channel surrounded by the outer wall or at an outflow end of the fluid channel surrounded by the outer wall.

15. The endoscope of claim 12, wherein the triangular base plane comprises an isosceles triangular base plane.

16. The endoscope of claim 12, wherein the fluid splitting element comprises a convex shaped side plane.

17. The endoscope of claim 1, wherein the fluid spray nozzle comprises an additional fluid channel/gas channel.

18. The endoscope of claim 17, wherein the additional fluid channel/gas channel is for a gas and is arranged laterally beside the fluid channel.

19. The endoscope of claim 1, wherein the fluid spray nozzle and the tip housing are monolithically formed in one-piece.

20. The endoscope of claim 1, wherein the tip housing comprises a recess, and wherein the fluid spray nozzle is received in the recess.

21. The endoscope of claim 20, wherein the fluid spray nozzle comprises a recess, and wherein the tip housing comprises a protrusion configured to engage the recess to align the fluid spray nozzle in the tip housing.

* * * * *